(12) United States Patent
McGrew et al.

(10) Patent No.: US 7,087,255 B2
(45) Date of Patent: Aug. 8, 2006

(54) CHEWING GUMS THAT PROVIDE BREATH FRESHENING CHARACTERISTICS

(75) Inventors: Gordon N. McGrew, Evanston, IL (US); James R. Maxwell, Chicago, IL (US); Henry T. Tyrpin, Palos Park, IL (US); Michael J. Greenberg, Northbrook, IL (US); David W. Record, River Forest, IL (US)

(73) Assignee: Wm. Wrigley Jr. Company, Chicago, IL (US)

(*) Notice: Subject to any disclaimer, the term of this patent is extended or adjusted under 35 U.S.C. 154(b) by 212 days.

(21) Appl. No.: 10/024,669

(22) Filed: Dec. 14, 2001

(65) Prior Publication Data

US 2002/0122843 A1    Sep. 5, 2002

(51) Int. Cl.
*A23G 4/06* (2006.01)
*A61K 9/68* (2006.01)

(52) U.S. Cl. .............................. 426/5; 424/48; 424/440
(58) Field of Classification Search ................ 426/3, 426/5; 424/48, 440
See application file for complete search history.

(56) References Cited

U.S. PATENT DOCUMENTS

| | | | |
|---|---|---|---|
| 2,677,700 A | 5/1954 | Jackson et al. |
| 3,639,563 A | 2/1972 | Januszewski |
| 3,947,570 A | 3/1976 | Pensak et al. |
| 4,130,636 A | 12/1978 | Tomlinson |
| 4,169,885 A | 10/1979 | Raaf et al. |
| 4,343,785 A | 8/1982 | Schmolka |
| 4,465,663 A | 8/1984 | Schmolka |
| 4,469,674 A | 9/1984 | Shah et al. |
| 4,476,107 A | 10/1984 | Schmolka |
| 4,511,563 A | 4/1985 | Schmolka |
| 4,664,906 A | 5/1987 | Sipos |
| 4,673,577 A | 6/1987 | Patel |
| 4,753,790 A | 6/1988 | Silva et al. |
| 4,792,453 A | 12/1988 | Reed et al. |
| 4,828,845 A | 5/1989 | Zamudio-Tena et al. |
| 5,154,927 A | 10/1992 | Song et al. |
| 5,165,944 A | 11/1992 | Song et al. |
| 5,248,508 A | 9/1993 | Reed et al. |
| 5,270,061 A | 12/1993 | Reed et al. |
| 5,286,500 A | 2/1994 | Synosky et al. |
| 5,376,389 A | 12/1994 | Reed et al. |
| 5,380,530 A | 1/1995 | Hill |
| 5,536,511 A | 7/1996 | Yatka |
| 5,603,907 A | 2/1997 | Grochowski |
| 5,702,687 A | 12/1997 | Miskewitz |
| 5,980,955 A | 11/1999 | Greenberg et al. |
| 6,030,605 A | 2/2000 | D'Ameila et al. |
| 6,121,315 A | 9/2000 | Nair et al. |

FOREIGN PATENT DOCUMENTS

WO    WO 00/35296    6/2000

*Primary Examiner*—Arthur L. Corbin
(74) *Attorney, Agent, or Firm*—Bell Boyd & Lloyd LLC

(57) ABSTRACT

A coated chewing gum is provided that includes a metal salt. The salt can be located in the gum center, coating, or both. A metal salt is provided in a therapeutically effective amount to reduce or eliminate oral malodors associated with bad breath. A variety of metal salts are possible. The coating may also include a surfactant and an edible oil.

35 Claims, No Drawings

CHEWING GUMS THAT PROVIDE BREATH FRESHENING CHARACTERISTICS

BACKGROUND OF THE INVENTION

The present invention relates generally to confectionery products. More specifically, the present invention relates to products that provide breath freshening properties and specifically chewing gums that provide breath freshening properties.

It is, of course, known to provide confectionery products for a variety of purposes. Typically these products provide a pleasant taste to the consumer. One such confectionery product is chewing gum.

Chewing gums that provide the consumer with a variety of flavors and characteristics are available. Typically chewing gum includes flavors and sweeteners. Flavors are designed to be released as the consumer chews the gum. There are a variety of types of chewing gums. For example, chewing gum can be provided in a shredded form, stick form, slab, ball, pellet, or other shapes and designs. It is also known to provide chewing gum that includes an outer coating. Typically, the outer coating is a hard shell that is either designed to dissolve in the mouth of the consumer or can be chewed. An example of such a product is a gumball.

Due to the release of flavor from the chewing gum during the chew, at least initially chewing gum can provide not only a pleasant taste to the consumer, but also breath freshening properties. In this regard, the release of flavor can mask mouth odors commonly referred to or associated with bad breath. However, typically, there is not sufficient flavor in the chewing gum to mask bad breath for an extended period of time and/or to mask more extreme odors that may be produced in cases of severe bad breath or associated with the ingestion of certain foods or other products.

It is known to use zinc and copper salts to reduce oral malodor. Zinc and copper salts work by bonding with volatile sulfur compounds that can be associated with bad breath. A number of products have been utilized to deliver these salts to the oral cavity. Such vehicles include mouthwash, candies, aerosol sprays, and even chewing gum.

One of the issues associated with the use of these metallic salts is their short, persistence time in the mouth. Such salts are quickly washed away by salivation or the consumption of a beverage. Another difficulty with such salts is they have a metallic taste. Additionally, there is an astringency associated with the metal.

A number of attempts have been made at addressing the problems associated with utilizing zinc and copper salts in oral compounds. One attempt is set forth in U.S. Pat. No. 6,030,605. In this patent, an edible oil and a surfactant of the metal salt is utilized in a chewing gum. The attempt is to increase retention time of the metal salt in the oral cavity. However, when the system is mixed into a chewing gum mass, it is not effectively released due to the hydrophobicity of the gum mass.

U.S. Pat. No. 6,121,315 attempts to address the problem of the taste of zinc and copper salts. In this regard, this patent includes cooling agents intended to mask the zinc flavor in a candy vehicle. However, when mixed into a gum mass, the hydrophobic gum base may reduce the effectiveness of this masking effect.

There is therefore a need for an improved chewing gum product that can provide metallic salts that provide breath freshening characteristics.

SUMMARY OF THE INVENTION

The present invention provides improved chewing gum products. More specifically, the present invention provides a coated chewing gum product that includes a metal salt that is designed to provide breath freshening to a consumer of the chewing gum.

To this end, in an embodiment, a chewing gum is provided comprising a gum center including a water-soluble portion and a water-insoluble portion and a coating that at least substantially surrounds the gum center, the coating includes a metal salt that is designed to provide breath freshening properties to a consumer of the chewing gum.

In an embodiment, the coating includes a surfactant. In a further embodiment, the surfactant is a non-ionic surfactant selected from the group consisting of poly ($C_2$–$C_4$-alkoxy) esters of $C_{18}$–$C_{20}$ fatty acids, $C_4$–$C_{20}$ alkyl poly ($C_2$–$C_4$-alkoxy) esters of $C_8$–$C_{20}$ fatty acids, poly ($C_2$–$C_4$ alkoxy) esters of sorbitan, poly ($C_2$–$C_4$ alkoxylated)-$C_1$–$C_{20}$ alcohols, polyethylene glycols, and mixtures thereof.

In an embodiment, the metal salt is chosen from the group consisting of zinc and copper.

In an embodiment, the metal salt includes a zinc salt selected from the group consisting of: zinc stearate; zinc acetate; zinc gluconate; zinc lactate; zinc ammonium sulfate; zinc chromate; zinc citrate; zinc dithionate; zinc fluorosilicate; zinc tartrate; zinc formate; zinc iodide; zinc nitrate; zinc phenol sulfonate; zinc salicylate; zinc sulfate; zinc succinate; zinc glycerophosphate; and zinc halides.

In an embodiment, the metal salt includes a copper salt selected from the group consisting of: copper stearate; copper acetate; copper gluconate; copper lactate; copper ammonium sulfate; copper chromate; copper citrate; copper dithionate; copper fluorosilicate; copper tartrate; copper formate; copper iodide; copper nitrate; copper phenol sulfonate; copper salicylate; copper sulfate; copper succinate; copper glycerophosphate; and copper halides.

In an embodiment, the coating includes an edible oil. In a further embodiment, the edible oil is a vegetable oil.

In an embodiment, the coating includes a cooling agent.

In an embodiment, the chewing gum includes at least one beneficial component selected from the group consisting of: fluoride salts; calcium salts; pyrophosphates; polyphosphates; antibacterial agents; cetylpyridinium chloride; chlorhexidine; essential oil mixtures containing menthol eucalyptol methyl salicylate, and thymol, botanical extracts such as sanguinaria; tooth desensitizing agents; potassium nitrate; plaque surface adhesion inhibitors; polydimethylsiloxane/surfactant; abrasive agents such as kaolin; silicas; surfactants; sodium laurel sulfate; and antibiotics.

In another embodiment of the present invention, a chewing gum product is provided comprising a metal salt, a gum center that includes a water-soluble portion, a water-insoluble portion, a coating surrounding the gum center, the coating including a cooling agent.

In an embodiment, the coating does not include any metal salt. In an embodiment, both the chewing gum center and coating include the metal salt.

In an embodiment, the coating includes a surfactant. In a further embodiment, the surfactant is a non-ionic surfactant selected from the group consisting of poly ($C_2$–$C_4$-alkoxy) esters of $C_{18}$–$C_{20}$ fatty acids, $C_4$–$C_{20}$ alkyl poly ($C_2$–$C_4$-alkoxy) esters of $C_8$–$C_{20}$ fatty acids, poly ($C_2$–$C_4$ alkoxy) esters of sorbitan, poly ($C_2$–$C_4$ alkoxylated)-$C_1$–$C_{20}$ alcohols, polyethylene glycols, and mixtures thereof.

In an embodiment, the coating includes an edible oil and a surfactant.

In a still further embodiment, a product that provides breath freshening properties to a consumer is provided. The product includes a gum center including a water-soluble portion and a water-insoluble portion. A coating surrounds the gum center. The coating includes a metal salt chosen from the group consisting of zinc and copper salts and a surfactant.

In yet another embodiment, a product that provides breath freshening properties is provided comprising a gum center including a water-soluble portion, a water-insoluble portion, and a metal salt chosen from the group consisting of zinc and copper salts. A coating surrounds the gum center and includes a cooling agent.

Still further, the present invention provides methods of treating halitosis. The method includes the steps of chewing a coated gum that includes a therapeutically effective amount of a metal salt. In an embodiment, the metal salt is zinc or copper.

An advantage of the present invention is to provide an improved chewing gum product.

Moreover, an advantage of the present invention is to provide an improved method for making a chewing gum product.

Furthermore, an advantage of the present invention is to provide an improved breath freshening product.

Still further, an advantage of the present invention is to provide a product for treating halitosis (bad breath).

Additionally, an advantage of the present invention is to provide a product that is designed to mask bad mouth odors that can be caused by bad breath, ingestion of certain foods, or products or other causes.

Still, an advantage of the present invention is to provide a method for orally delivering metal salts to a consumer.

Furthermore, an advantage of the present invention is to provide a chewing gum product including metal salts that is palatable to the consumer.

Additional features and advantages of the present invention will be described in and apparent from the detailed description of the presently preferred embodiments.

DETAILED DESCRIPTION OF THE PRESENTLY PREFERRED EMBODIMENTS

The present invention provides improved coated chewing gum products.

Specifically, the present invention provides products that provide breath freshening properties to the consumer. As used herein, the term "breath freshening" refers to the ability to at least temporarily mask an effective portion of odors that are produced from the mouth of the consumer. These odors can be due to a variety of causes. Halitosis, or bad breath, may be produced from ingestion or inhalation of substances that are excreted in part by the lungs, from gingivial or dental disease, from fermentation of food particles in the mouth, or may be associated with systemic diseases. To "provide breath freshening characteristics" means that the product at least alleviates the severity of the halitosis for at least a limited time.

Pursuant to the present invention, a coated chewing gum is provided that includes a metal salt. As set forth below, the salt can be located in the gum center, coating, or both. A metal salt is provided in a therapeutically effective amount to reduce or eliminate oral malodors. Thus, in an embodiment, the present invention provides a method of treating halitosis. A variety of metal salts are possible. Preferably, the metal salts are food acceptable salts of zinc and copper.

In an embodiment, the salt is a zinc salt. By way of example, the zinc salt may be selected from the group of salts consisting of: zinc stearate; zinc acetate; zinc gluconate; zinc lactate; zinc ammonium sulfate; zinc chromate; zinc citrate; zinc dithionate; zinc fluorosilicate; zinc tartrate; zinc formate; zinc iodide; zinc nitrate; zinc phenol sulfonate; zinc salicylate; zinc sulfate; zinc succinate; zinc glycerophosphate; and zinc halides. In an embodiment, the zinc salts for use in the present invention are zinc gluconate and zinc lactate.

In addition to zinc salts, copper salts can be utilized. The copper salt can be selected from the group consisting of: copper stearate; copper acetate; copper gluconate; copper lactate; copper ammonium sulfate; copper chromate; copper citrate; copper dithionate; copper fluorosilicate; copper tartrate; copper formate; copper iodide; copper nitrate; copper phenol sulfonate; copper salicylate; copper sulfate; copper succinate; copper glycerophosphate; and copper halides.

If desired, more than one zinc and/or copper salt can be used.

As noted above, the chewing gum is a coated chewing gum. In this regard, the chewing gum product includes a gum center and a coating that surrounds the gum center.

A variety of different coatings can be utilized. In part, the coating is typically composed primarily of a sugar or sugar alcohol or a mixture of sugars and sugar alcohols. As discussed below, pursuant to the present invention, the coating can include other agents. Typically, the coating is applied as a solution, utilizing a coating drum, on to the gum center. Usually a process is used that includes evaporation of water in the syrup to leave a dry coating. In such processes, typically multiple layers of such a coating are applied often with applications of dry powdered material being applied between coats of syrup.

In addition to the ingredients set forth below, numerous other minor constituents may be added to the syrup or powder to provide desirable, functional, or sensory benefits. These ingredients include: binders; film-forming agents; high-intensity sweeteners; inorganic fillers; colors; polishing agents; flavors; acids; and the like.

A variety of coating systems can be utilized in the present invention. Examples of such systems are set forth in U.S. Pat. Nos.: 4,753,790; 4,828,845; 4,792,453; 5,248,508; 5,270,061; 5,376,389; 5,536,511; and 5,603,907 the disclosures of all of which are incorporated herein by reference.

In an embodiment of the present invention, the chewing gum comprises a coated chewing gum including a metallic salt, a surfactant or emulsifier, and an edible oil in the coating.

The oil component of the present invention includes any physiologically acceptable oil, particularly any edible vegetable oil. As used herein, the term "vegetable oil" includes any edible vegetable oil. These oils are triglycerides of fatty acids in which the acyl portions generally contain 8 to 24 carbon atoms and zero to three carbon-carbon double bonds. The term vegetable oil as used herein also includes naturally occurring oils which have been purified and/or modified, for instance by bleaching or by partial or complete hydrogenation. Oils useful in this invention are liquid at ambient temperatures. An example of an oil that can be used is canola oil. Other suitable oils include the low calorie oil based on short and long chain fatty acids which is known by its trade designation Salatrim (Cultor) and medium chain triglyceride compounds of capric and caprylic acids, an example of such is Liponate GC from Lipo Chemicals. Suitable oils also include soybean oil and corn oil.

The oil component can be present in the coating in amounts from 0.1% to 10.0% by weight of the coating, preferably 0.2% to 3.0% by weight of the coating.

With respect to the surfactant, a variety of surfactants or mixtures of surfactants can be used. Suitable surfactants include nonionic, anionic, amphoteric and cationic surfactants. Examples of suitable non-ionic surfactant include: poly ($C_2$–$C_4$-alkoxy) esters, and particularly polyoxyethylene esters, of $C_8$–$C_{20}$ fatty acids, such as polyethyleneglycol oleate and polyethyleneglycol stearate; $C_4$–$C_{20}$ alkyl polyglycol ether carboxylates of $C_8$–$C_{20}$ carboxylic acids including the compounds described in U.S. Pat. No. 4,130,636, which is incorporated herein by reference; poly ($C_2$–$C_4$-alkoxy) esters, and particularly polyoxyethylene esters of sorbitan, such as those described in U.S. Pat. Nos. 3,639,563 and 3,947,570, which are incorporated herein by reference; poly ($C_2$–$C_4$-alkoxylated) and particularly poly (propoxylated) $C_1$–$C_{20}$, alcohols such as an acetyl alcohol, including those described in U.S. Pat No. 2,677,700, which is incorporated herein by reference; and polyethylene glycols.

Other suitable surfactants include block copolymers comprising a congeneric mixture of conjugated polyoxypropylene and polyoxyethylene compounds having as a hydrophobe, a polyoxypropylene polymer of at least 1200 molecular weight, such as those described in U.S. Pat. Nos. 4,343,785, 4,465,663, 4,511,563 and 4,476,107, which are incorporated herein by reference.

The polymers are prepared by adding the required number of moles of propylene oxide to the two hydroxyl groups of propylene glycol to form a hydrophobic base and then adding ethylene oxide to both ends of the hydrophobic base to form hydrophilic polyoxyethylene groups of controlled length.

Some preferred polymers are the commercially available surfactants which include the polyoxyethylene-polyoxypropylene block copolymers and the non-ionic polyoxypropylene-polyoxyethylene block co-polymers or poloxamers. These polymers have a molecular weight range of 500 to 30,000 and are of the general formula:

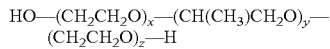

wherein x is 2–128, y is 16–67 and z is 2–128.

The surfactant is present in the coating of the present invention from about 0.1% to 10.0% by weight, preferably 0.5% to 3.0% by weight.

The coating of the present invention is prepared by thoroughly mixing together the coating syrup, divalent cationic component, the oil, and the non-ionic surfactant.

In an embodiment of the present invention, the chewing gum includes a cooling agent in the coating. Suitable cooling agents include: menthol; monomenthyl succinate and salts thereof; cyclic carboxamides such as WS3; acyclic carboxamides such as WS23; menthyl acetate; menthyl lactate; menthone ketals; 3-menthoxypropane-1,2 diol (Takasago cooling agent); and mixtures thereof.

In addition to these products, the chewing gum may include other beneficial agents including: fluoride salts; calcium salts; phosphates including pyrophosphates and polyphosphates; antibacterial agents such as Triclosan; cetylpyridinium chloride; chlorhexidine; and essential oil mixtures such as those containing menthol, eucalyptol, methyl salicylate, and thymol; botanical extracts such as sanguinaria; tooth desensitizing agents such as potassium nitrate; plaque surface adhesion inhibitors such as polydimethylsiloxane/surfactant; abrasive agents such as kaolin and silicas; surfactants such as sodium laurel sulfate; antibiotics; and the like.

The chewing gum center of the present invention, aside from including the ingredients set forth above, can be a variety of products. Chewing gum generally consists of a water insoluble gum base, a water soluble portion, and flavor. The water soluble portion dissipates with a portion of the flavor of the gum over a period of time during chewing. The gum base portion is retained in the mouth throughout the chew.

The insoluble gum base generally comprises elastomers, resins, fats and oils, softeners and inorganic fillers. The gum base may or may not include wax. Typically, gum base comprises approximately 20 to about 40% of the gum product. However, because in the present invention such a high level of coating may be used, the gum center is typically unusually small; otherwise the entire coating chewing gum piece would be too large for consumption. If a typical amount of gum base was used in the small gum center, it would result in an inadequate cud to masticate. Consequently, in the present invention, the base level is higher than normal. The insoluble gum base can constitute approximately 30% to about 90% by weight of the chewing gum, in an embodiment, the gum base comprises at least 50% of the chewing gum.

In an embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate-vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10–45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium dioxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof.

Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high-intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, galactose, corn syrup solids, and the like, alone or in combination. Sugarless sweeteners include, but are not limited to, sugar alcohols such as sorbitol, mannitol, xylitol, hydrogenated starch hydrolysates, maltitol, erythritol, and the like, alone or in combination.

High-intensity artificial sweeteners can also be used, alone or in combination, with the above. Preferred sweeteners include, but are not limited to, sucralose, aspartame, salts of acesulfame, altitame, saccharin and its salts, cyclamic acid and its salts, glycerrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low calorie bulking agent can be used. Examples of low calorie bulking agents include: polydextrose; Raftilose, Raftilin; Fructooligosaccharides (NutraFlora); Palatinose oligosaccharide; Guar Gum Hydrolysate (Sun Fiber); or indigestible dextrin (Fibersol). However, other low calorie bulking agents can be used.

A variety of flavoring agents can also be used, if desired. The flavor can be used in amounts of approximately 0.1 to about 15 weight percent of the gum, and preferably, approximately 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

The gum center can be prepared using a variety of different methods and machinery known in the art. For example, the formulation can be mixed using a sigma blade mixer. The center formulation may also be made by continuous processing equipment known in the art. Conventional sheeting and scoring machinery can be used to form and score the centers or the centers can be made on a forming machine that involves a drop frame and nitrogen cooling allowing spheres, ovals, and other shapes to be made.

By way of example and not limitations, examples of the present invention will now be given:

EXAMPLES 1 and 2

Chewing gum centers were prepared by mixing the following ingredients and forming pillow shaped pellets.

|  | Example 1 | Example 2 |
|---|---|---|
| Sorbitol | 51.51% | 49.85% |
| Gum Base | 27.83 | 27.83 |
| Talc | 4.92 | 4.92 |
| Lemon Flavor | 2.37 | 2.37 |
| Encapsulated Food Acids | 2.37 | 2.37 |
| Malic Acid | 1.67 | 1.67 |
| Zinc Gluconate | 1.50 | 3.00 |
| Citric Acid | 0.83 | 0.83 |
| Encapsulated APM | 1.13 | 1.13 |
| WS23 | 0.20 | 0.20 |
| Lecithin | 0.20 | 0.20 |
| Cooling Agent Mixture | — | 0.16 |
| Glycerin | 5.47 | 5.47 |
|  | 100.00 | 100.00 |

EXAMPLE 3

Coatings were then applied to the centers of Examples 1 and 2. All components except the wax were dissolved or dispersed to create a 70–75% solids solution in hot water. The syrup was applied to the pellets in a conventional coating apparatus to produce a coating level of approximately 34.5%. Finally, the pellets were polished with the wax.

|  | Example 3 |
|---|---|
| Maltitol | 90.3544 |
| Gum Acacia | 7.4127 |
| Lemon Flavor | 0.9400 |
| Color | 0.6000 |
| WS23 | 0.2600 |

-continued

| | Example 3 |
|---|---|
| APM | 0.1513 |
| Talc | 0.1643 |
| Carnauba Wax | 0.1173 |
| | 100.0000 |

The cooling agent in the coating helps mask the high level of zinc in the center.

EXAMPLES 4–6

Chewing gum centers are made as before (see Example Nos 1–2) using these formulas.

| | Example 4 | Example 5 | Example 6 |
|---|---|---|---|
| Gum Base | 24.00 | 27.00 | 30.00 |
| Sugar | 52.30 | 51.90 | 45.10 |
| Corn Syrup | 20.00 | 19.00 | 18.00 |
| Peppermint Flavor | 1.00 | — | 0.70 |
| Wintergreen Flavor | — | 1.00 | 0.80 |
| Aspartame | — | — | 0.40 |
| Glycerin | 0.20 | 0.40 | 1.00 |
| Zinc Gluconate | 1.50 | — | 1.50 |
| Zinc Lactate | — | — | 1.00 |
| Copper Gluconate | 0.50 | 0.70 | 0.50 |
| Menthol | 0.50 | 0.70 | 1.00 |
| | 100.00 | 100.00 | 100.00 |

EXAMPLES 7–9

The gum centers of Examples 4–6 are each coated with each of the following compositions in a Driam or Dumoulin coater as before (see Example No. 3).

| | Example 7 | Example 8 | Example 9 |
|---|---|---|---|
| Starch | 5.00 | 4.00 | 6.00 |
| Sugar | 92.83 | 92.45 | 89.25 |
| Peppermint Flavor | 0.50 | 1.00 | 1.50 |
| Menthol | 0.50 | 0.30 | — |
| WS-23 | 0.02 | — | — |
| Methyl Succinate | 0.15 | 0.10 | 0.25 |
| Menthone Glycerol Ketal | — | 0.15 | — |
| Zinc/Oil/Surfactant* | 1.00 | 2.00 | 3.00 |
| | 100.00 | 100.00 | 100.00 |

*A premix containing 30% Zinc Gluconate, 35% Pluronic F108 (BASF) and 35% coconut oil.

After coating, the pellets were polished with carnauba wax. The samples will exhibit prolonged breath freshening and metallic off-notes will be reduced.

EXAMPLES 10–13

Gum centers are mixed and formed as before (Examples No. 1–2) using the following formulas.

| | Example 10 | Example 11 | Example 12 | Example 13 |
|---|---|---|---|---|
| Gum Base | 40.00 | 44.60 | 35.00 | 40.00 |
| Sorbitol | 35.60 | 29.21 | 44.20 | — |
| Xylitol | — | — | — | 43.95 |
| Filler (CaCO$_3$) | 15.00 | 14.90 | 10.00 | 10.00 |
| Glycerin | 3.50 | 4.00 | 4.00 | 0.10 |
| Wintergreen Flavor | 3.00 | 3.50 | 3.00 | 2.00 |
| Water | — | 0.90 | 0.90 | 0.90 |
| Encapsulated APM | 1.50 | 1.90 | 2.00 | 1.40 |
| APM | 0.20 | 0.10 | — | 0.10 |
| WS3 | 0.10 | — | 0.25 | 0.10 |
| Menthyl Glycol Carbonate | — | 0.01 | — | 0.01 |
| Menthyl Propylene Glycol Carbonate | — | 0.01 | — | 0.01 |
| Menthyl Lactate | — | 0.01 | — | — |
| Menthyl Succinate | — | — | — | 0.40 |
| Menthol | — | 0.01 | 0.20 | 0.40 |
| Takasago Cooling Agent | 0.10 | — | 0.10 | 0.05 |
| WS23 | — | 0.10 | 0.10 | — |
| Zinc Gluconate | 0.50 | 0.75 | — | 0.35 |
| Copper Gluconate | — | — | 0.25 | — |
| Zinc Chloride | — | — | — | 0.25 |
| Copper Lactate | 0.50 | — | — | — |
| | 100.00 | 100.00 | 100.00 | 100.00 |

EXAMPLES 14–17

Each of the gum centers from Examples 10–13 are coated as before (Example No. 3) using each of the following coating compositions.

| | Example 14 | Example 15 | Example 16 | Example 17 |
|---|---|---|---|---|
| Maltitol | 91.34 | 90.23 | 86.88 | 91.85 |
| Gum Acacia | 5.00 | 6.00 | 7.00 | 4.00 |
| Color | .01 | .02 | .01 | .01 |
| Wintergreen Flavor | .50 | .50 | 1.00 | 2.00 |
| APM | .10 | .15 | — | .10 |
| Menthyl Succinate | .02 | .04 | .02 | .01 |
| Menthone Glycerol Ketal | .01 | .01 | .04 | — |
| Menthyl Lactate | — | .02 | .01 | — |
| WS3 | .01 | .01 | — | .01 |
| WS23 | — | .01 | .02 | 02 |
| Menthyl Glycol Carbonate | .01 | — | .01 | — |
| Menthol Propylene Glycol Carbonate | — | .01 | .01 | — |
| Metal/Oil/Surfactant 1** | 3.00 | — | 2.00 | — |
| Metal/Oil/Surfactant 2** | — | 3.00 | — | 2.00 |
| Metal/Oil/Surfactant 3** | — | — | 3.00 | — |
| | 100.00 | 100.00 | 100.00 | 100.00 |

**The Metal/Oil/Surfactant components are premixes constituted as follows:
1  10% Zinc Lactate, 60% palm oil, 30% Tween 40 (Hercules)
2  15% Zinc Gluconate, 50% hydrogenated cottonseed oil, 35% Tween 80 (Hercules)
3  15% Copper Gluconate, 45% hydrogenated soybean oil, 40% Pluronic F127 (BASF)

After coating, the pellets are polished with carnauba wax. The samples will exhibit prolonged breath freshening properties with minimal off-taste and astringency.

EXAMPLES 18–21

Examples 14–17 are repeated except that xylitol is substituted for maltitol in Examples 14 and 15 and palatinit is substituted for maltitol in Examples 16 and 17.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A chewing gum comprising:
a coated gum center, wherein the gum center and coating each includes a metal salt that provides breath freshening characteristics to a consumer of the chewing gum, wherein said metal salt is selected from the group consisting of food acceptable zinc and copper salts.

2. The chewing gum of claim 1 wherein the coating includes a surfactant.

3. The chewing gum of claim 2 wherein the surfactant is a non-ionic surfactant selected from the group consisting of poly ($C_2$–$C_4$-alkoxy) esters of $C_{18}$–$C_{20}$ fatty acids, $C_4$–$C_{20}$ alkyl poly ($C_2$–$C_4$-alkoxy) esters of $C_8$–$C_{20}$ fatty acids, poly ($C_2$–$C_4$ alkoxy) esters of sorbitan, poly ($C_2$–$C_4$ alkoxylated)-$C_1$–$C_{20}$ alcohols, polyethylene glycols, and mixtures thereof.

4. The chewing gum of claim 2 wherein the coating includes an edible oil.

5. The chewing gum of claim 4 wherein the edible oil is a vegetable oil.

6. The chewing gum of claim 1 wherein the metal salt includes a zinc salt selected from the group consisting of: zinc stearate; zinc acetate; zinc gluconate; zinc lactate; zinc ammonium sulfate; zinc chromate; zinc citrate; zinc dithionate; zinc fluorosilicate; zinc tartrate; zinc formate; zinc nitrate; zinc phenol sulfonate; zinc salicylate; zinc sulfate; zinc succinate; zinc glycerophosphate; and zinc halides.

7. The chewing gum of claim 1 wherein the metal salt includes a copper salt selected from the group consisting of: copper stearate; copper acetate; copper gluconate; copper lactate; copper ammonium sulfate; copper chromate; copper citrate; copper dithionate; copper fluorosilicate; copper tartrate; copper formate; copper nitrate; copper phenol sulfonate; copper salicylate; copper sulfate; copper succinate; copper glycerophosphate; and copper halides.

8. The chewing gum of claim 1 wherein the coating includes a cooling agent.

9. The chewing gum of claim 8 wherein the cooling agent is selected from the group consisting of: menthol; monomenthyl succinate and salts thereof; cyclic carboxamides; acyclic carboxamides; menthyl acetate; menthyl lactate; menthone ketals; 3-menthoxypropane-1,2 diol; and mixtures thereof.

10. The chewing gum of claim 1 including at least one beneficial component selected from the group consisting of: fluoride salts; calcium salts; pyrophosphates; polyphosphates; antibacterial agents; cetylpyridinium chloride; chlorhexidine; essential oil mixtures containing menthol, eucalyptol, methyl salicylate, and thymol; botanical extracts; tooth desensitizing agents; potassium nitrate; plaque surface adhesion inhibitors; polydimethylsiloxane/surfactant; abrasive agents; silicas; surfactants; sodium laurel sulfate; and antibiotics.

11. A chewing gum product comprising:
a metal salt that is provides breath freshening characteristics to a consumer of the chewing gum product and being selected from the group consisting of food acceptable zinc and copper salts;
a gum center including a water-soluble portion, a water-insoluble portion, wherein the gum center includes the metal salt; and
a coating surrounding the gum center, including a cooling agent and the metal salt.

12. The chewing gum of claim 11 wherein the coating includes a surfactant.

13. The chewing gum of claim 12 wherein the surfactant is a non-ionic surfactant selected from the group consisting of poly ($C_2$–$C_4$-alkoxy) esters of $C_{18}$–$C_{20}$ fatty acids, $C_4$–$C_{20}$ alkyl poly ($C_2$–$C_4$-alkoxy) esters of $C_8$–$C_{20}$ fatty acids, poly ($C_2$–$C_4$ alkoxy) esters of sorbitan, poly ($C_2$–$C_4$ alkoxylated)-$C_1$–$C_{20}$ alcohols, polyethylene glycols, and mixtures thereof.

14. The chewing gum of claim 11 wherein the metal salt includes a zinc salt selected from the group consisting of: zinc stearate; zinc acetate; zinc gluconate; zinc lactate; zinc ammonium sulfate; zinc chromate; zinc citrate; zinc dithionate; zinc fluorosilicate; zinc tartrate; zinc formate; zinc nitrate; zinc phenol sulfonate; zinc salicylate; zinc sulfate; zinc succinate; zinc glycerophosphate; and zinc halides.

15. The chewing gum of claim 11 wherein the metal salt includes a copper salt selected from the group consisting of: copper stearate; copper acetate; copper gluconate; copper lactate; copper ammonium sulfate; copper chromate; copper citrate; copper dithionate; copper fluorosilicate; copper tartrate; copper formate; copper nitrate; copper phenol sulfonate; copper salicylate; copper sulfate; copper succinate; copper glycerophosphate; and copper halides.

16. The chewing gum of claim 11 wherein the coating includes an edible oil.

17. A chewing gum product containing a metal salt designed that provides breath freshening properties to a consumer of the chewing gum product, comprising:
a gum center including a metal salt selected from the group consisting of food acceptable zinc and copper salts, a water-soluble portion, a water-insoluble portion; and
a coating surrounding the gum center, including a cooling agent and a metal salt selected from the group consisting of zinc and copper salts.

18. The chewing gum of claim 17 wherein the coating includes an edible oil.

19. The chewing gum of claim 17 wherein the metal salt includes a zinc salt selected from the group consisting of: zinc stearate; zinc acetate; zinc gluconate; zinc lactate; zinc ammonium sulfate; zinc chromate; zinc citrate; zinc dithionate; zinc fluorosilicate; zinc tartrate; zinc formate; zinc nitrate; zinc phenol sulfonate; zinc salicylate; zinc sulfate; zinc succinate; zinc glycerophosphate; and zinc halides.

20. The chewing gum of claim 17 wherein the metal salt includes a copper salt selected from the group consisting of: copper stearate; copper acetate; copper gluconate; copper lactate; copper ammonium sulfate; copper chromate; copper citrate; copper dithionate; copper fluorosilicate; copper tartrate; copper formate; copper nitrate; copper phenol sulfonate; copper salicylate; copper sulfate; copper succinate; copper glycerophosphate; and copper halides.

21. The chewing gum of claim 17 wherein the cooling agent is selected from the group consisting of: menthol; monomenthyl succinate and salts thereof; cyclic carboxamides; acyclic carboxamides; menthyl acetate; menthyl lactate; menthone ketals; 3-menthoxypropane-1,2 diol; and mixtures thereof.

22. The chewing gum of claim 17 including at least one beneficial component selected from the group consisting of: fluoride salts; calcium salts; pyrophosphates; polyphosphates; antibacterial agents; cetylpyridinium chloride; chlorhexidine; essential oil mixtures containing menthol, eucalyptol, methyl salicylate, and thymol; botanical extracts; tooth desensitizing agents; potassium nitrate; plaque surface adhesion inhibitors; polydimethylsiloxane/surfactant; abrasive agents; silicas; surfactants; sodium laurel sulfate; and antibiotics.

23. The chewing gum product of claim 17 wherein the coating includes a surfactant.

24. The chewing gum product of claim 23 wherein the surfactant is a non-ionic surfactant selected from the group consisting of poly ($C_2$–$C_4$-alkoxy) esters of $C_{18}$–$C_{20}$ fatty acids, $C_4$–$C_{20}$ alkyl poly ($C_2$–$C_4$-alkoxy) esters of $C_8$–$C_{20}$ fatty acids, poly ($C_2$–$C_4$ alkoxy) esters of sorbitan, poly ($C_2$–$C_4$ alkoxylated)-$C_1$–$C_{20}$ alcohols, polyethylene glycols, and mixtures thereof.

25. A method for treating halitosis comprising the steps of chewing a chewing gum comprising a coated gum center including a water-soluble portion a water-insoluble portion, wherein the coating at least substantially surrounds the gum center, the coating and gum center each including a therapeutically effective amount of with a metal salt that provides breath freshening characteristics, to a consumer of the chewing gum, wherein said metal salt is selected form the group consisting of food acceptable zinc and copper salts being a therapeutically effective amount.

26. The method of treating halitosis of claim 25, wherein the gum further includes, in the coating surrounding the gum center, a cooling agent.

27. A chewing gum product comprising:
a coated gum center including a water-soluble portion, a water-insoluble portion and a copper salt that provides breath freshening characteristics to a consumer of the chewing gum product; and
a coating surrounding the gum center and including a copper salt that provides breath freshening characteristics to a consumer of the chewing gum product.

28. The chewing gum product of claim 27 wherein the copper salt is selected from the group consisting of: copper stearate; copper acetate; copper gluconate; copper lactate; copper ammonium sulfate; copper chromate; copper citrate; copper dithionate; copper fluorosilicate; copper tartrate; copper formate; copper nitrate; copper phenol sulfonate; copper salicylate; copper sulfate; copper succinate; copper glycerophosphate; and copper halides.

29. The chewing gum product of claim 27 wherein the coating includes an edible oil.

30. The chewing gum product of claim 27 wherein the coating includes a cooling agent.

31. The chewing gum of claim 30 wherein the cooling agent is selected from the group consisting of: menthol; monomenthyl succinate and salts thereof; cyclic carboxamides; acyclic carboxamides; menthyl acetate; menthyl lactate; menthone ketals; 3-menthoxypropane-1,2 diol; and mixtures thereof.

32. The chewing gum product of claim 27 wherein the gum center includes a zinc salt selected from the group consisting of: zinc stearate; zinc acetate; zinc gluconate; zinc lactate; zinc ammonium sulfate; zinc chromate; zinc citrate; zinc dithionate; zinc fluorosilicate; zinc tartrate; zinc formate; zinc nitrate; zinc phenol sulfonate; zinc salicylate; zinc sulfate; zinc succinate; zinc glycerophosphate; and zinc halides.

33. The chewing gum product of claim 27 including at least one beneficial component selected from the group consisting of: fluoride salts; calcium salts; pyrophosphates; polyphosphates; antibacterial agents; cetylpyridinium chloride; chlorhexidine; essential oil mixtures containing menthol, eucalyptol, methyl salicylate, and thymol; botanical extracts; tooth desensitizing agents; potassium nitrate; plaque surface adhesion inhibitors; polydimethylsiloxane/surfactant; abrasive agents; silicas; surfactants; sodium laurel sulfate; and antibiotics.

34. The chewing gum product of claim 27 wherein the coating includes a surfactant.

35. The chewing gum product of claim 34 wherein the surfactant is a non-ionic surfactant selected from the group consisting of poly ($C_2$–$C_4$-alkoxy) esters of $C_{18}$–$C_{20}$ fatty acids, $C_4$–$C_{20}$ alkyl poly ($C_2$–$C_4$-alkoxy) esters of $C_8$–$C_{20}$ fatty acids, poly ($C_2$–$C_4$ alkoxy) esters of sorbitan, poly ($C_2$–$C_4$ alkoxylated)-$C_1$–$C_{20}$ alcohols, polyethylene glycols, and mixtures thereof.

* * * * *